United States Patent
Tabatabaei (10) Patent No.: US 12,239,855 B2
(45) Date of Patent: Mar. 4, 2025

(54) mmWAVE ARRAY AND IMPLANTED SUSCEPTORS FOR HYPERTHERMIA-BASED ANTI-CANCER TREATMENTS

(71) Applicant: mmTron Inc., Redwood City, CA (US)

(72) Inventor: Seyed A Tabatabaei, Half Moon Bay, CA (US)

(73) Assignee: mmTron Inc.

( * ) Notice: Subject to any disclaimer, the term of this patent is extended or adjusted under 35 U.S.C. 154(b) by 173 days.

(21) Appl. No.: 18/117,376

(22) Filed: Mar. 3, 2023

(65) Prior Publication Data
US 2024/0293684 A1 Sep. 5, 2024

(51) Int. Cl.
*A61N 7/02* (2006.01)
*A61N 7/00* (2006.01)

(52) U.S. Cl.
CPC ........ *A61N 7/02* (2013.01); *A61N 2007/0004* (2013.01); *A61N 2007/0095* (2013.01); *A61N 2007/025* (2013.01)

(58) Field of Classification Search
CPC .... A61N 5/02; A61N 5/022; A61N 2005/027; A61N 5/04
See application file for complete search history.

(56) References Cited

U.S. PATENT DOCUMENTS

| | | | |
|---|---|---|---|
| 4,876,737 A * | 10/1989 | Woodworth | H04B 7/18517 455/12.1 |
| 11,349,223 B2 | 5/2022 | Corman et al. | |
| 2005/0261570 A1 | 11/2005 | Mate et al. | |
| 2008/0269851 A1 * | 10/2008 | Deem | A61N 5/04 607/104 |
| 2010/0036369 A1 * | 2/2010 | Hancock | A61B 18/1815 606/33 |

FOREIGN PATENT DOCUMENTS

| CA | 2741948 | * | 12/2011 |
|---|---|---|---|
| WO | WO 2009126571 | * | 10/2009 |

OTHER PUBLICATIONS

Yao et al (CN 113713169) machine translation (Year: 2021).*
Mahmoud, Korany R., and Ahmed M. Montaser. "Design of Hyperthermia Applicator to Heat Multi-Brain Tumors Simultaneously Based on Adaptive Beamforming Technique." IEEE Journal of Electromagnetics, RF and Microwaves in Medicine and Biology 5.2 (2020): 115-123.

(Continued)

*Primary Examiner* — Alexei Bykhovski
(74) *Attorney, Agent, or Firm* — Daylight Law, P.C.

(57) ABSTRACT

Methods and systems for hyperthermia-based anti-cancer treatments are disclosed herein. One disclosed system for hyperthermia-based anti-cancer treatments includes an array of millimeter wave amplifier integrated circuits having an output energy, one or more medical grade implantable susceptors, and a beam steering controller for the array of millimeter wave amplifier integrated circuits that is configured to steer the output energy of the array of millimeter wave amplifier integrated circuits into the one or more medical grade implantable susceptors.

18 Claims, 5 Drawing Sheets

(56) References Cited

OTHER PUBLICATIONS

Phong Thanh Nguyen, Amin M. Abbosh, and Stuart Crozier. "3-D Focused Microwave Hyperthermia for Breast Cancer Treatment With Experimental Validation." IEEE Transactions On Antennas And Propagation, vol. 65, No. 7, Jul. 2017: 3489-3500.

Rosa Orlacchio, Denys Nikolayev, Yann Le Page, Yves Le Dréan, and Maxim Zhadobov. "Millimeter-Wave Heating In Vitro: Local Microscale Temperature Measurements Correlated to Heat Shock Cellular Response". IEEE Transactions On Biomedical Engineering, vol. 69, No. 2, Feb. 2022: 840-848.

\* cited by examiner

FIG. 6 mmWAVE ARRAY AND IMPLANTED SUSCEPTORS FOR HYPERTHERMIA-BASED ANTI-CANCER TREATMENTS

BACKGROUND

Non-invasive radiation treatment for cancer has a long history, with early forms of external beam radiation therapy being developed in the early 1900s. Over the years, advancements in technology have led to significant improvements in the accuracy and effectiveness of non-invasive radiation treatments, such as intensity-modulated radiation therapy (IMRT) and image-guided radiation therapy (IGRT). These newer forms of non-invasive radiation treatment allow for higher doses of radiation to be delivered to cancerous tumors with greater precision and with fewer side effects to healthy surrounding tissues. Additionally, the development of proton therapy has added another non-invasive option for cancer treatment, which uses protons instead of photons or electrons to deliver the radiation. Non-invasive radiation treatment is now a well-established part of the cancer treatment landscape, offering patients a range of options for receiving effective and minimally invasive cancer care.

Non-invasive hyperthermia treatments for cancer have also made significant strides in recent decades. Hyperthermia involves the use of heat to destroy cancer cells and has been used in combination with radiation therapy to enhance its effectiveness. Early forms of hyperthermia involved the use of hot water baths or heating pads, but technological advancements have led to the development of non-invasive methods such as microwave and radiofrequency hyperthermia. These non-invasive methods allow for targeted heating of the tumor without damaging surrounding healthy tissue, making them a promising addition to the cancer treatment arsenal. As with non-invasive radiation treatment, the development of more precise and effective non-invasive hyperthermia treatments offers patients a range of options for receiving care that minimizes the impact on their quality of life.

SUMMARY

This disclosure relates to methods for using radio frequency energy for anti-cancer treatments. Specific embodiments of the inventions disclosed herein relate to methods and systems for using a mmWave array and implanted susceptors for hyperthermia-based anti-cancer treatments. As used in this disclosure, the term mmWave refers to frequencies that are in the range of 30 GHz to 200 GHz. In contrast to microwave energy, these frequencies exhibit less power but greater resolution. Specific embodiments of the inventions disclosed herein use arrays of mmWave to accurately steer energy to implanted medical grade susceptors for hyperthermia-based anti-cancer treatments. The use of both mmWave energy and array-based beam steering results in a system that is both precise in its targeting to assure minimal damage to healthy tissue. Combined with the use of medical grade implanted susceptors, the resulting system is furthermore able to precisely deliver a sufficient and desired level of thermal energy to achieve beneficial clinical outcomes.

As used in this disclosure, the term "medical grade implantable" refers to devices designed and manufactured to be implanted into the human body for the purpose of medical treatment. These devices are typically subject to regulatory requirements and must meet rigorous standards for safety, performance, and biocompatibility. Examples of medical grade implantable devices include pacemakers, implantable cardioverter defibrillators (ICDs), spinal cord stimulators, cochlear implants, and drug delivery pumps. The term "medical grade" implies that these devices are of a higher quality and reliability than those intended for other purposes, and that they have undergone extensive testing and evaluation to ensure their safety and efficacy for medical use.

In specific embodiments of the inventions disclosed herein, a system for hyperthermia-based anti-cancer treatments is provided. The system comprises an array of millimeter wave amplifier integrated circuits having an output energy, one or more medical grade implantable susceptors, and a beam steering controller for the array of millimeter wave amplifier integrated circuits that is configured to steer the output energy of the array of millimeter wave amplifier integrated circuits into the one or more medical grade implantable susceptors.

In specific embodiments of the inventions disclosed herein, a method for hyperthermia-based anti-cancer is provided. The method comprises implanting one or more medical grade susceptors sub-dermally in the body of a patient, generating, using an array of millimeter wave amplifier integrated circuits, an output energy, steering, in a steering step and using a beam steering controller for the array of millimeter wave amplifier integrated circuits, the output energy of the array of millimeter wave amplifier integrated circuits into the one or more medical grade susceptors.

BRIEF DESCRIPTION OF THE DRAWINGS

The accompanying drawings illustrate various embodiments of systems, methods, and embodiments of various other aspects of the disclosure. A person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles FIG. 1 provides a flow chart for a set of methods for using a mmWave array and implanted susceptors for hyperthermia-based anti-cancer treatments in accordance with specific embodiments of the inventions disclosed herein.

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Different components and methods for a hyperthermia-based anti-cancer treatment will be described in detail in this disclosure. The methods and systems disclosed in this section are nonlimiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

A system for hyperthermia-based anti-cancer treatment is disclosed herein. The system comprises an array of millimeter wave amplifier integrated circuits configured to emit an output energy. The output energy is a total output energy of the array of millimeter wave amplifier integrated circuits. The output energy is in the millimeter (mm) wave energy with a frequency range of 30 to 220 gigahertz. It can be noted that the array of millimeter wave amplifier integrated circuits is an array of D band amplifiers. The output energy is electromagnetic wave energy with frequencies between 20 gigahertz and one terahertz. Further, the system comprises one or more medical grade susceptors implanted over a target area of a user. The one or more medical grade susceptors comprises a susceptor body, a temperature sensor integrated to the susceptor body, a radio transmitting module coupled to the temperature sensor, a wireless inductive power source, and a polymer coating layered over the susceptor body, the temperature sensor, and the radio transmitting module. The susceptor body is formed of stainless steel and titanium material. The wireless inductive power source is charged by the output energy. The radio transmitting module may correspond to one or more radio frequency transmitters.

Further, the system comprises a beam steering controller linked to the array of millimeter wave amplifier integrated circuits. The beam steering controller is configured to steer the output energy of the array of millimeter wave amplifier integrated circuits into the one or more medical grade implantable susceptors. In one embodiment, the beam steering controller is configured to steer at least 97% of total output energy of the array of millimeter wave amplifier integrated circuits into the one or more medical grade implantable susceptors. Further, the beam steering controller is configured to adjust the output energy using information from the one or more temperature sensors. The information corresponds to real-time temperature of the one or more medical grade susceptors, and real-time temperature of surrounding tissue. In specific embodiments of the invention, the adjusting is conducted to minimize the application of the output energy to health tissue and involves minimizing the application of the output energy to tissue of the patient using the information while still applying sufficient energy to tumor cells of the patient to achieve denaturation of the tumor cells and eventual cell death or a cessation of cell mitosis.

In another aspect of the present invention, a method for hyperthermia-based anti-cancer treatment, is disclosed. The method comprises steps as: at first, one or more medical grade susceptors are implanted sub-dermally over a target area into the user. Further, an output energy is generated using an array of millimeter wave amplifier integrated circuits. Successively, the output energy is steered, in a steering step by the beam steering controller, and emitted into the one or more medical grade susceptors. Successively, infrared radiating heat is generated at the one or more medical grade susceptors in response to the output energy steered. Further, target cells over the target area of the user are deactivated or destroyed using the generated infrared radiating heat energy.

Figure 1:
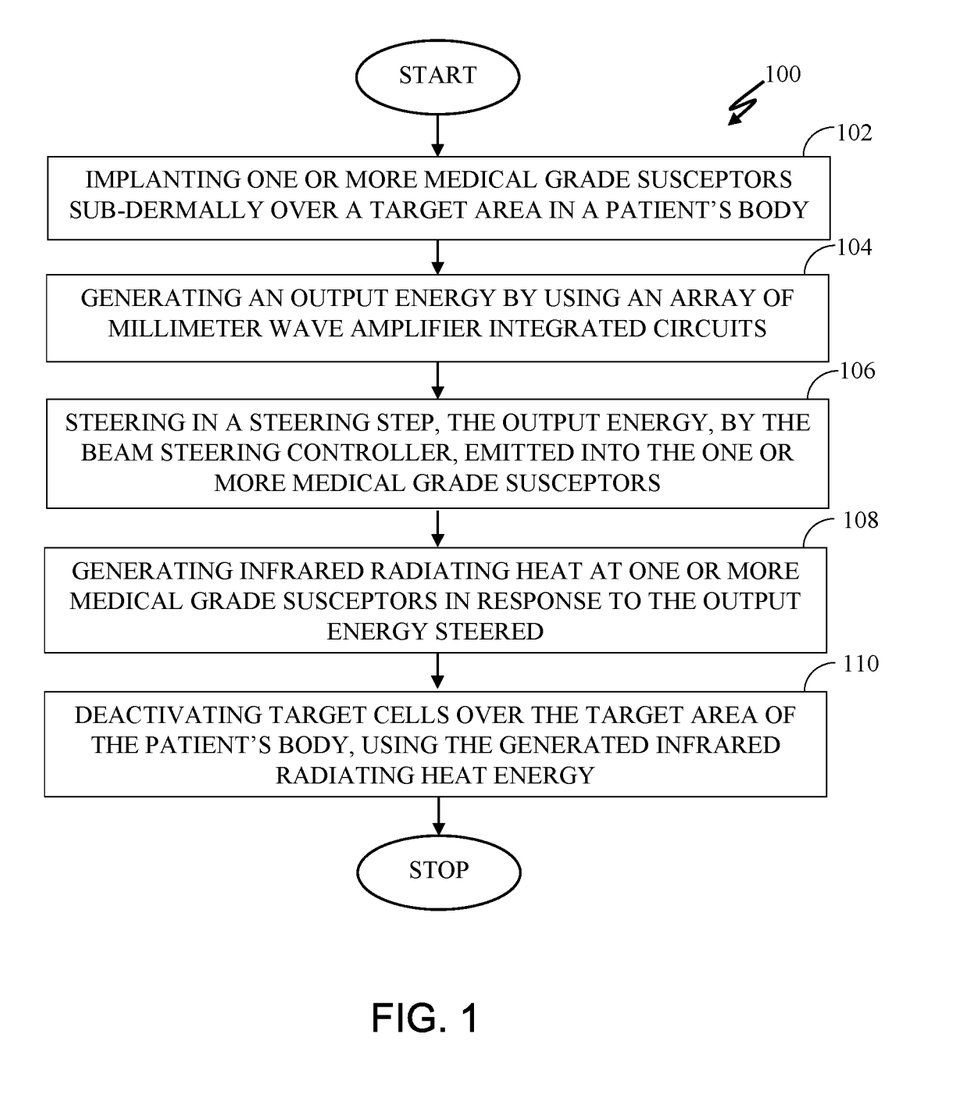

FIG. 1 illustrates a flowchart of a method 100 for hyperthermia-based anti-cancer treatment, according to an embodiment.

At first, one or more medical grade susceptors are implanted sub-dermally over a target area into a user, at step 102. In one embodiment, the user may be a patient undergoing specific treatment. For example, Mark carrying a brain tumor of the glioblastoma multiforme (GBM) type over the cerebrum region, is implanted with 2 susceptors sub-dermally over the cerebrum region.

Successively, an output energy is generated using an array of millimeter wave amplifier integrated circuits, at step 104. For example, a millimeter wave amplifier integrated circuit is installed over the head region of Mark. The millimeter wave amplifier integrated circuit carries 6 antenna bands for transmitting millimeter waves at 42.4 Giga Hertz (GHz) for 30 minutes.

Successively, the output energy is steered in a steering step by the beam steering controller, to be emitted into the one or more medical grade susceptors, at step 106. For example, a beam steering controller receives the transmitted millimeter waves at 42.4 GHz from the millimeter wave amplifier integrated circuits. The beam steering controller concentrates the beam (mm waves) received from the millimeter wave amplifier integrated circuit towards the 2 implanted susceptors over the cerebrum region.

Successively, infrared radiating heat is generated at the one or more medical grade susceptors in response to the output energy steered, at step 108. For example, the implanted susceptors converts the received concentrated mm wave into infrared radiating heat energy. The implanted susceptors is heated and reaches up to a temperature of 42° Celsius or 107.6° Fahrenheit.

Successively, target cells over the target area of the user are deactivated or destroyed using the generated infrared radiating heat energy, at step 110. For example, the heated up 2 implanted susceptors also increases the temperature of the cancer cells in the brain tumor of the GBM type. The 2 implanted susceptors increases the temperature of the cancer cells up to 40° to 42° Celsius to kill the cancer cells and thereby leaving healthy cells unharmed.

Figure 2:
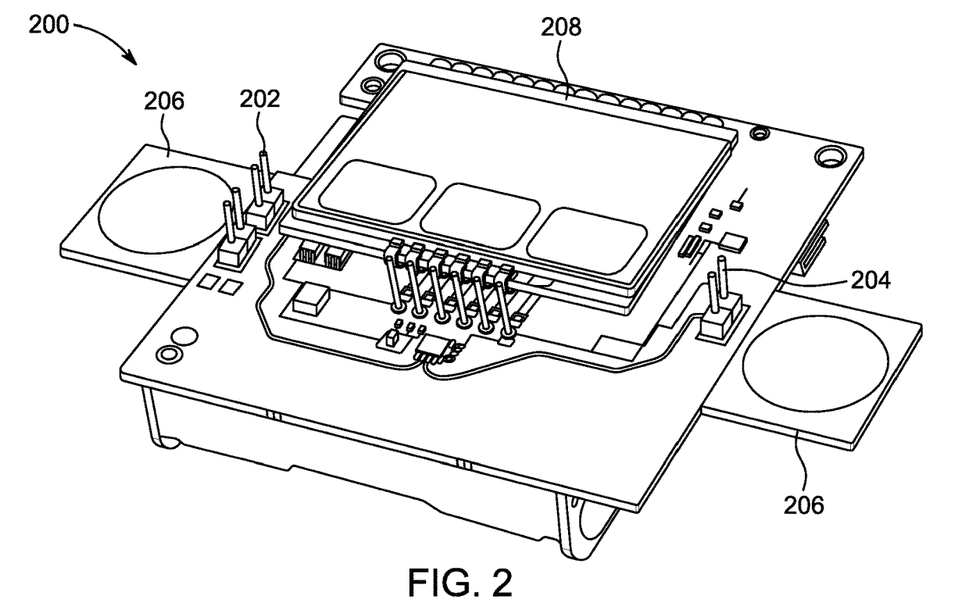
FIG. 2 provides a perspective view of a millimeter wave amplifier integrated circuit in accordance with specific embodiments of the inventions disclosed herein.

FIG. 2 illustrates a perspective view of a millimeter wave amplifier integrated circuit assembly 200, according to an embodiment. FIG. 2 will be described in conjunction with FIG. 3.

In one embodiment, the millimeter wave amplifier integrated circuit assembly 200 is a device or module that boosts or increases the power of a radio frequency signal. The assembly includes a millimeter wave amplifier integrated circuit 208, a supporting substrate, and accompanying circuit elements such as antennas. The millimeter wave amplifier integrated circuit enhances the radio frequency signal or increases input power to produce greater power at the output. Typically, the millimeter wave amplifier integrated circuit assembly 200 includes active and passive elements that may increase voltage or current level of a signal. In one exemplary embodiment, the millimeter wave amplifier integrated circuit is integrated with a transistor and three-terminal semiconductor devices that may gain current, such that a minor change in current results in a pro-rated change in the integrated circuit amplifier output.

Further, the millimeter wave amplifier integrated circuit assembly 200 comprises one or more receiving (RX) antenna 202, one or more transmitting (TX) antenna 204, a pair of nodes 206, a memory (not shown). The one or more TX antennas 202 and the one or more RX antennas 204 may be fabricated over a substrate (not shown) in a suitable configuration. In one exemplary embodiment, at least two TX antennas and at least four RX antennas are fabricated over the substrate. The one or more TX antennas 202 and the one or more RX antennas 204 may correspond to a circuitry arrangement (not shown) over the substrate. The one or more (TX) antenna 204 may be configured to transmit the millimeter waves at a predefined frequency via the pair of nodes 206. The millimeter wave amplifier integrated circuit assembly 200 is configured to emit millimeter (mm) waves at a pre-defined frequency. For example, the millimeter wave amplifier integrated circuit assembly 200 emits millimeters wave signals of frequency range between 30 GHz to 300 GHz.

In one embodiment, the memory may include suitable logic, circuitry, and/or interfaces that may be configured to store a machine code and/or a computer program with at least one code section executable by a controller. The controller can be integrated with the millimeter wave amplifier integrated circuit 208, a separate microprocessor or microcontroller on the same substrate as millimeter wave amplifier integrated circuit 208, or a separate device that can communicated with the millimeter wave amplifier integrated circuit. Examples of implementation of the memory may include, but are not limited to, Random Access Memory (RAM), Read Only Memory (ROM), Hard Disk Drive (HDD), and/or a Secure Digital (SD) card. Further, the controller may facilitate operation of the one or more receiving (RX) antenna 202 and the one or more transmitting (TX) antenna 204 to perform functions according to the instructions stored in the memory. In one embodiment, the controller may include suitable logic, circuitry, interfaces, and/or code, that may be configured to execute a set of instructions stored in the memory. The controller may be configured to run the instructions obtained by a control system (not shown) to generate the required mm waves. The control system is described in conjunction with FIG. 6.

In specific embodiments of the invention, a millimeter wave amplifier integrated circuit assembly can include an array of millimeter wave amplifier integrated circuits. The elements of the array can be individual millimeter wave amplifier integrated circuits. For example, the array can be a set of two or more millimeter wave amplifier integrated circuits can be located on a printed circuit board. Each element of the array can include its own antennas and each can independently transmit and/or receive millimeter wave energy. The array can be a regular or irregular array of individual elements. According to specific embodiments of the inventions disclosed herein, the various elements of the array can participate in steering of the energy generated by the array by changing their relative energy output and altering the pattern of coherence and interference of the millimeter wave integrated circuits produced by each element. The elements of the array can be arranged with irregular or regular spacing. The elements of the array can be arranged in lines and columns, in a spiral, in a circle, and in various other configurations.

The amplified millimeter wave transmitted by the millimeter wave amplifier integrated circuit assembly 200 is controlled by a beam steering controller (not shown). The beam steering controller is configured to steer the output energy of the array of millimeter wave amplifier integrated circuits into the one or more medical grade implantable susceptors. The beam steering controller can be a microprocessor or microcontroller integrated on the same substrate as the millimeter wave amplifier integrated circuits. Alternatively, the beam steering controller can be an external device that communicates with a local controller of the millimeter wave amplifier integrated circuits using a PCI Express, of TP-Link connection. In one embodiment, the beam steering controller is able to control one or more radiating elements (e.g., the antennas of one or more millimeter wave amplifier integrated circuit assemblies). The one or more radiating elements are configured to radiate elements transmitting at various frequencies, amplitudes, and phases. The frequency and phases of the individual signals can be modified by the beam steering controller to produce targeted radiation patterns owing to the coherence and interference of the various signals.

In one embodiment, the beam steering controller changes the phase of an input signal on the one or more radiating elements. Phase shifting allows the input signal to be targeted at a specific receiver module (not shown) at a target location. The beam steering controller can employ radiating elements with a common frequency to steer a single beam in a specific direction. In one embodiment, multiple frequency beams may also be steered in different directions to serve different users. It can be noted that the direction of the signals can be calculated in real-time by a the beam steering controller using the approaches disclosed herein. In one embodiment, the beam steering controller is configured to process and calculate the direction at which the signal is to be directed.

In one exemplary embodiment, the millimeter wave amplifier integrated circuit may be a TMC774 D-band chip. In one embodiment, TMC774 D-band chip is configured to transit radio frequencies at the range of 110 GHz to 170 GHz in an electromagnetic spectrum corresponding to a recommended frequency band of operation of WR6 and WR7 waveguides. In one embodiment, these frequencies are equivalent to wavelengths between 2.7 mm and 1.8 mm.

Figure 3:
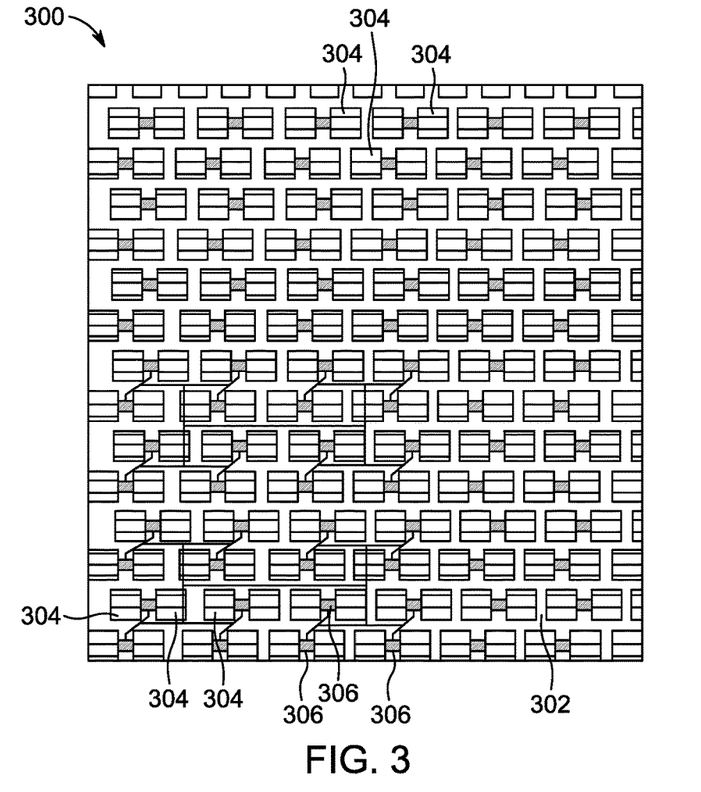
FIG. 3 provides a schematic view of an array of the millimeter wave amplified integrated circuit in accordance with specific embodiments of the inventions disclosed herein.

FIG. 3 illustrates a schematic view of an array of the millimeter wave amplified integrated circuits 300, according to an embodiment. The array of the millimeter wave amplified integrated circuits 300 comprises a printed circuit board 302, one or more patch antennas 304 and one or more integrated circuits 306.

In one embodiment, the printed circuit board 302 may comprise several signal paths, each connected to the one or more patch antennas 304 and the one or more integrated circuits 306. In one embodiment, the one or more patch antennas 304 may comprise one or more pairs of RX antennas and one or more pair of TX antennas that may be configured in parallel arrangement.

In one embodiment, the one or more patch antennas 304 may be oriented in a triangulation patch array configuration, a rectangular lattice configuration, a pentagonal configuration or a hexagonal configuration. In one embodiment, the printed circuit board 302 may be incorporated with a ground plane (not shown) that is configured to cooperate with the one or more patch antennas 304 to initiate directed operation.

In one embodiment, the one or more patch antennas 304 may be integrated over a flat surface (not shown) and includes a flat rectangular sheet of metal (not shown) mounted over the ground plane. In one embodiment, a dielectric layer may be sandwiched between the flat rectangular sheet and the ground plane to isolate the two layers from conduction. Under energization, the one or more patch antennas 304 and the ground plane produce a radiating electric filed.

It may be noted that the one or more pair of RX antennas and the one or more pair of TX antennas may also be arranged in different spatial antenna arrays in different configurations. In one embodiment, the array of millimeter wave amplified integrated circuit 300 may be formed in one, two, or even three dimensions, with one or a two-dimensional array being more common.

Figure 4:
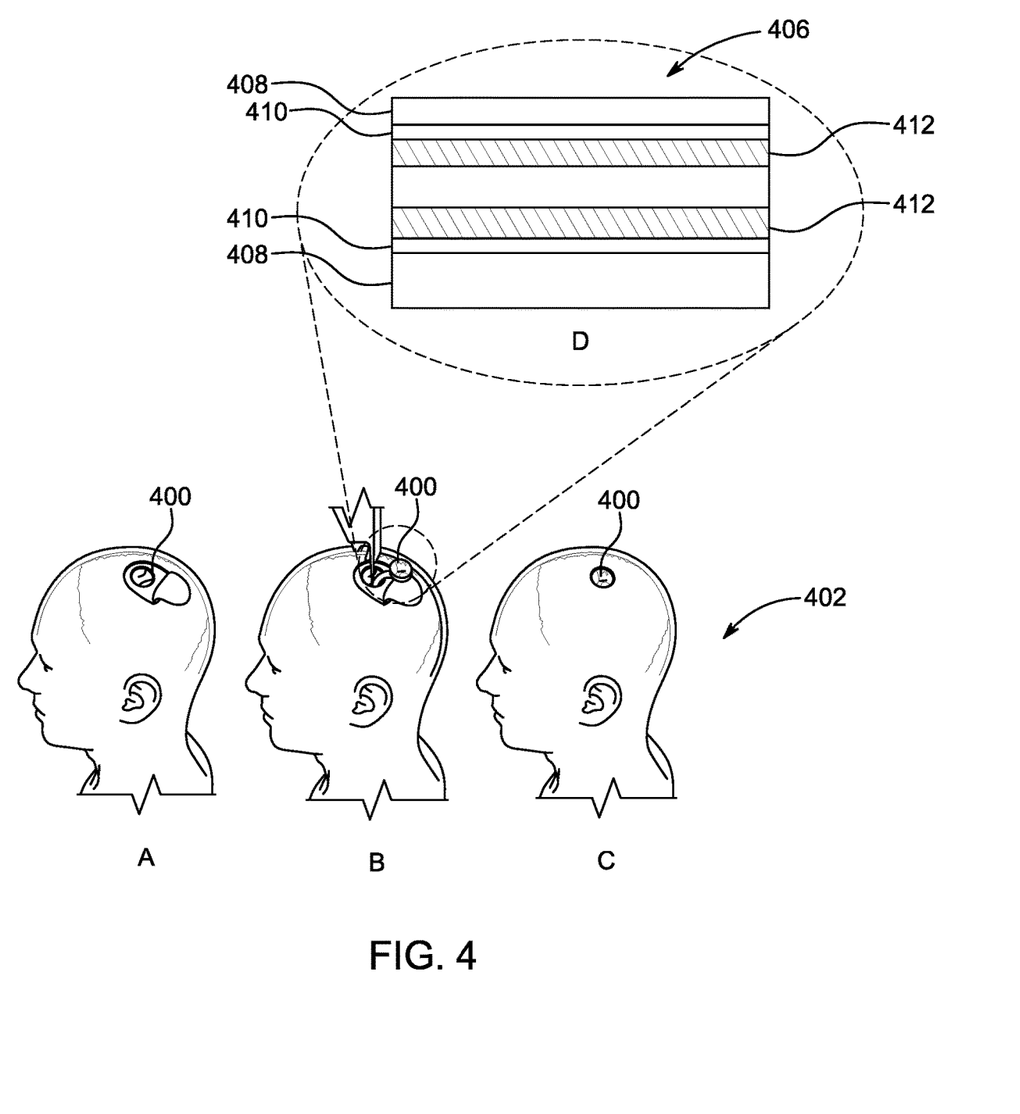
FIG. 4 provides perspective views of one or more medical grade susceptors implanted into a user and an enlarged sectional view of the one or more medical grade susceptors implanted into the user in accordance with specific embodiments of the inventions disclosed herein.

FIG. 4 illustrates perspective views of one or more medical grade susceptors 400 implanted into a user 402, according to an embodiment. FIG. 4 is divided into four views labeled A, B, C, and D. FIG. 4 can be described in conjunction with FIG. 5.

In one embodiment, the one or more medical grade susceptors 400 are capable of generating heat via magnetic hysteresis losses in the presence of an energy source, such as millimeter (mm) waves. In other embodiments, the one or more medical grade susceptors 400 are capable of generating heat via induction heating as an external magnetic field causes eddy currents in the susceptor to generate heat when interacting with the resistance of the material. In another embodiment, the one or more medical grade susceptors 400 are capable of generating heat via dielectric heating in the presence of an energy source, such as millimeter (mm) waves. In these embodiments, the molecules of the susceptor generate heat in response to their rotation in the alternating electric field in which they are placed when energy is applied from an external source.

In one embodiment, the one or more medical grade susceptors 400 are medical grade implantable and are made of medical grade materials. In one embodiment, the one or more medical grade susceptors 400 may be made from a material selected from a group of materials of ceramics, aluminum, titanium, or other user compatible metals and non-metals. In one embodiment, the term medical grade implantable refers to devices designed and manufactured to be implanted into the user 402 for the purpose of medical treatment. These devices are typically subject to regulatory requirements and must meet rigorous standards for safety, performance, and biocompatibility. Examples of medical grade implantable devices include pacemakers, implantable cardioverter defibrillators (ICDs), spinal cord stimulators, cochlear implants, and drug delivery pumps. Further, the term medical grade implies that these devices are of a higher quality and reliability than those intended for other purposes, and that they have undergone extensive testing and evaluation to ensure their safety and efficacy for medical use.

In specific embodiments, the one or more medical grade susceptors 400 may have various shapes such as flat circular elements that are arranged to be normal to an electric field generated by an external energy source. In specific embodiments, the elements can range in size from a radius of 0.5 centimeters to a radius of 5 centimeters. The elements can also have customized sizes which are generate for a specific patient in order to match a desired pattern of heat delivery. Further, the one or more medical grade susceptors 400 may be directly disposed over a solid tumor over which the millimeter (mm) waves may be imparted, causing tumor cell denaturation in the body of the patient using the convection heat energy.

The one or more medical grade susceptors 400 may be implanted sub-dermally over the cerebrum region. The operation of implanting the one or more medical grade susceptors 400, is shown in FIG. 4. Firstly, a cavity 404 may be formed precisely over the area where tumor is formed. Successively, the one or more medical grade susceptors 400 may be implanted inside the cavity 404. Further, the cavity 404 may be sealed securely such that the millimeter (mm) waves may now be imparted over the one or more medical grade susceptors 400. The one or more medical grade susceptors 400 in the tumor may display a collective energized state that causes heating and ablation of the tumor tissue, resulting in a reduction or removal of the tumor tissue.

In one exemplary embodiment, any type of cancer may be treated by using the one or more medical grade susceptors 400 that may exhibit a collective energized state. In one embodiment, localized solid tumors such as those of the skin, head and neck, tongue, throat, larynx, brain, breast, liver, pancreas, lymph nodes, joint or synovium, uterine or cervix, peritoneum, or other particular organs may also be treated.

FIG. 4 section D illustrates an enlarged sectional view of the one or more medical grade susceptors 400. In one embodiment, the one or more medical grade susceptors 400 may be fabricated with multiple layers. The one or more medical grade susceptors 400 may comprise a susceptor body 406, cover layers 408, adhesive layers 410 and polymer coatings 412. In one embodiment, the one or more medical grade susceptors 400 may comprise the susceptor body 406. The susceptor body 406 may be made up of stainless steel and titanium material. Further, the one or more medical grade susceptors 400 may also be made up of variety of materials, including but not limited to magnetite ($Fe_3O_4$), maghemite (—$Fe_2O_3$), and $FeCo/SiO_2$. In some embodiments, the one or more medical grade susceptors 400 may also be made of aggregates of superparamagnetic grains made of materials like $Co_{36}C_{65}$, $Bi_3Fe_5O_{12}$, $BaFe_{12}O_{19}$, NiFe, CoNiFe etc.

In one embodiment, the cover layers 408 may be configured to encase the remainder of the layers of the one or more medical grade susceptors 400. In one embodiment, the cover layers 408 may be made up of a polymer material, ceramic material, or other type of support material which is dimensionally stable through a temperature ranging up to several hundred degrees Celsius.

In one embodiment, the adhesive layers 410 may be configured to adhere the multiple layers of the one or more medical grade susceptors 400. In one embodiment, the adhesive layers 410 may be a high temperature structural epoxy resin adhesive. The high temperature structural epoxy resin adhesive may help the adhesive layers 410 to maintain structural rigidity of the one or more medical grade susceptors 400 under high degree temperatures when imparted with continuous millimeter (mm) waves. In one embodiment, the polymer coatings 412 may be used to improve the thermal conductivity of the one or more medical grade susceptors 400.

Figure 5:
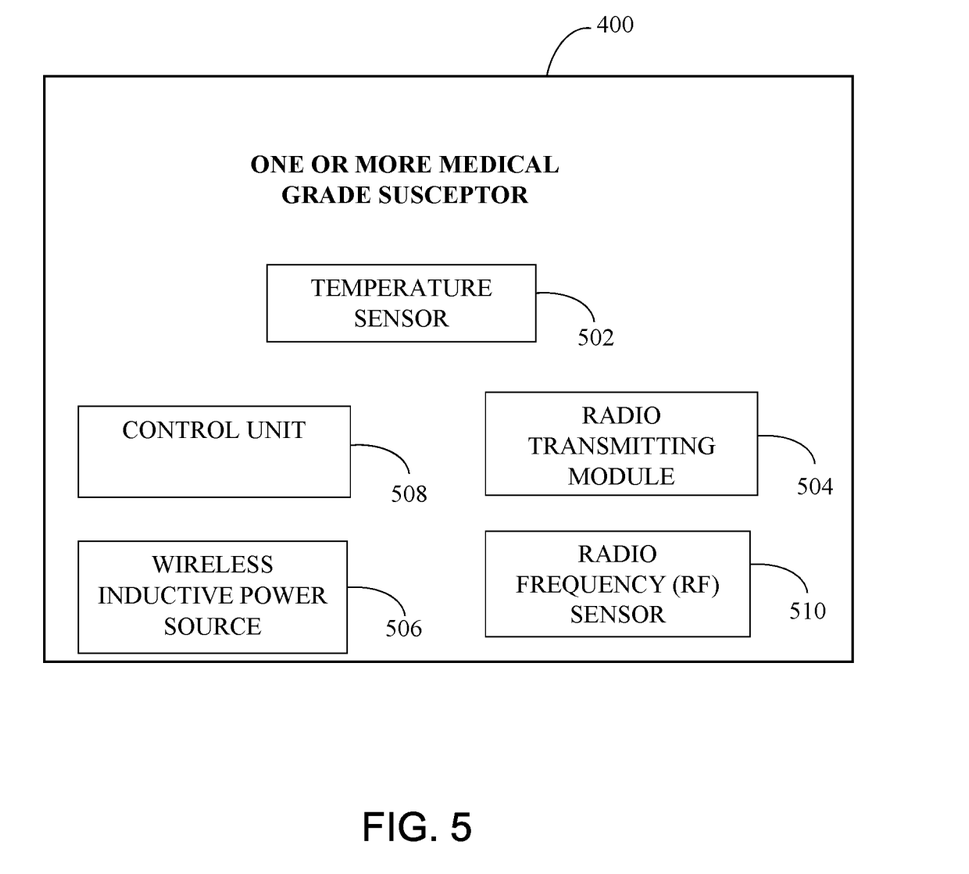
FIG. 5 illustrates a block diagram of the one or more medical grade susceptors in accordance with specific embodiments of the inventions disclosed herein.

FIG. 5 illustrates a block diagram of the one or more medical grade susceptors 400, according to an embodiment.

In one embodiment, the one or more medical grade susceptors 400 may comprise of a temperature sensor 502, a radio transmitting module 504, a wireless inductive power source 506, a control unit 508, a radio frequency (RF) sensor 510. The radio transmitting module can include a radio transmitter.

In one embodiment, the temperature sensor 502 may be configured to measure real-time temperature of the target area of the user 402. The temperature sensor 502 monitors the temperature of the tissue surrounding the one or more medical grade susceptors 400 and helps to ensure that the heat generated is at a safe and therapeutic level. The temperature rises due to the generation of convection heat energy by the one or more medical grade susceptors 400 in response to the received mm wave in the steering step 106.

In one embodiment, the radio transmitting module 504 may be configured to transmit temperature information gathered by the temperature sensor 502. For example, the temperature sensor 502 measures temperature of the tissue surrounding the one or more medical grade susceptors 400 is 47° Celsius. The radio transmitting module 504 collects this information and send signals in the form of radio waves.

In one embodiment, the wireless inductive power source 506 may be configured to receive the millimeter waves and generate electrical energy to power the temperature sensor 502 and the radio transmitting module 504. In one embodiment, the control unit 508 may work as a bridge between the temperature sensor 502 and the radio transmitting module 504. The information generated by the temperature sensor 502 may be in the form of electrical signals. The control unit 508 may be configured to convert those electrical signals into a readable format information. The information may include the temperature measurement. The control unit 508 may communicate the information further wirelessly with the help of radio transmitting module 504.

In one embodiment, the RF sensor 510 is configured to determine the amount of radiation received by the one or more medical grade susceptors 400. It can be noted that the RF sensor 510 is an antenna (not shown) having an analog front end amplifier (not shown) that measures the amount of electromagnetic energy received by detecting the amplitude of the radio wave. The antenna collects the electromagnetic wave, which is then converted into an electrical signal by the analog front end amplifier. The one or more medical grade susceptors 400 measures the strength of the electrical signal, which is proportional to the amplitude of the incoming electromagnetic wave. It can be noted that the amount of energy being absorbed is derived based on this amplitude measurement. This information can then be fed back to the external controller to guide the adjusting of the energy applied to the patient in a feedback loop.

In one embodiment, the analog front end amplifier may also be configured to measure the frequency of the energy absorbed by the one or more medical grade susceptors 400 to provide a more accurate estimate of the absorbed energy. The array of millimeter wave amplifier integrated circuits 300 may be configured to transmit mm Wave energy at a fixed frequency, such that the frequency is known and the one or more medical grade susceptors 400 do not need to be designed to measure frequency in order to determine the amount of energy applied to the susceptor (e.g., only an amplitude measurement is sufficient). However, in alternative approaches, the frequency applied can vary such that the measurement of the amount of radiation received by the one or more medical grade susceptors 400 is based on a measurement of the frequency of the energy absorbed. Once the amount of energy has been calculated using both the frequency and the amplitude, this information can be fed back to the external controller to guide the adjusting of the energy applied to the patient in a feedback loop.

In another embodiments, the one or more medical grade susceptors 400 may transmit temperature information to the external controller in a feedback system to reach a target temperature in the vicinity of the medical grade susceptor 400. The temperature information can be the temperature of the temperature sensor on the susceptor. This information can then be fed back to the external controller to guide the adjusting of the energy applied to the patient in a feedback loop to reach the target temperature.

Further, the temperature sensor 502, the radio transmitting module 504, the wireless inductive power source 506, the control unit 508 and the RF sensor 510 may be coated with the polymer coatings 412. In one embodiment, the polymer coatings 412 improves the thermal conductivity of the one or more medical grade susceptors 400. The polymer coatings 412 may be chains of polymer molecules made by joining together many small molecules called monomers that are made up of a large number of similar units. In one embodiment, the thermal conductivity of the polymer coatings 412 is between 0.1 and 0.5 W m−1 K−1 due to their amorphous state.

Figure 6:
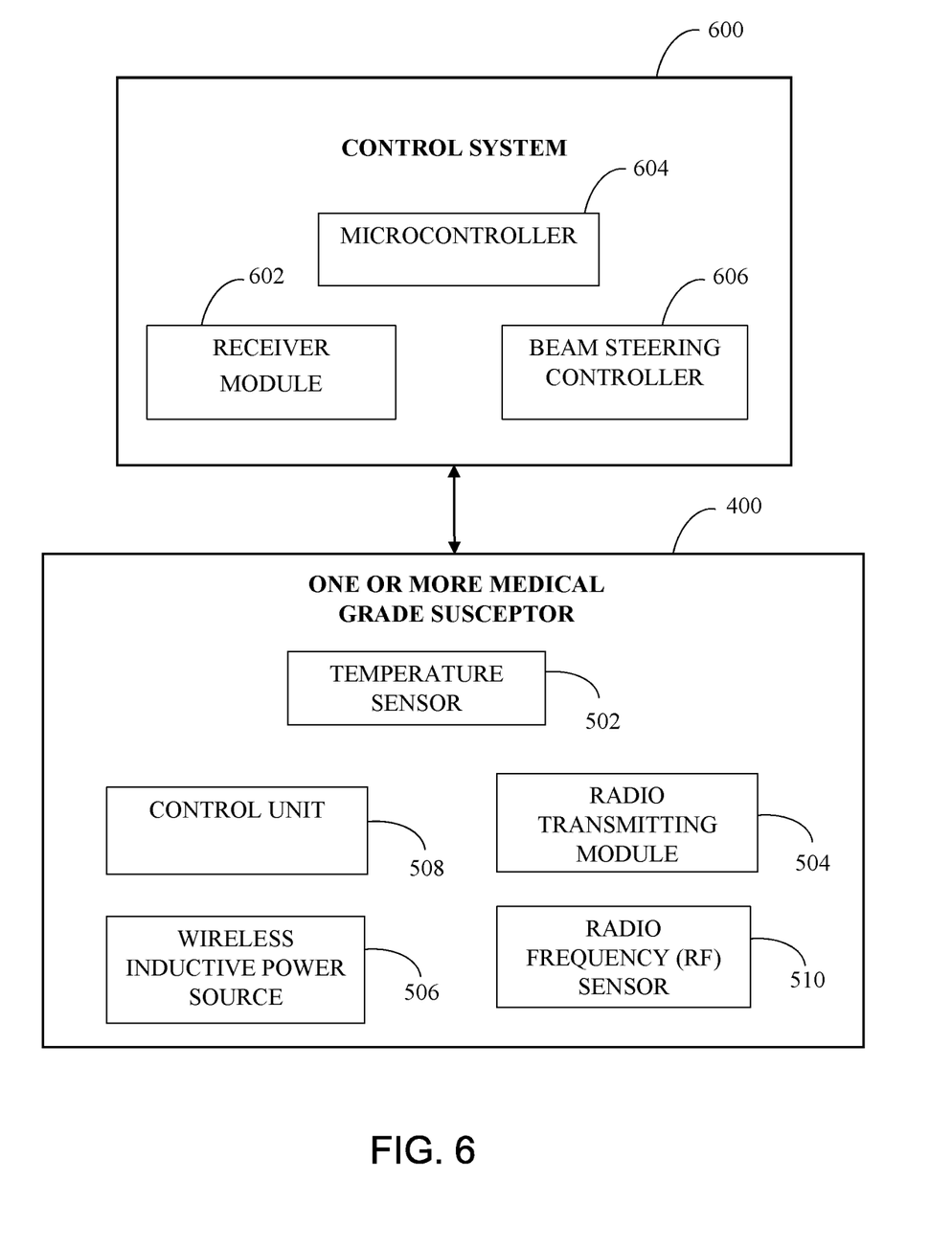
FIG. 6 illustrates a block diagram of communication establishment between the one or more medical grade susceptors and a control system in accordance with specific embodiments of the inventions disclosed herein.

FIG. 6 illustrates a block diagram of communication establishment between the one or more medical grade susceptors 400 and a control system 600, according to an embodiment.

The control system 600 may comprise a receiver module 602, a microcontroller 604 and a beam steering controller 606. As discussed, the control system 600 may be configured to receive the information transmitted by the radio transmitting module 504 and the amount of radiation received by the one or more medical grade susceptors 400. Further, the beam steering controller 606, based upon the received information, adjusts the pattern of interference and coherence while broadcasting the millimeter waves received from output energy of the millimeter wave amplifier integrated circuit to adjust and regulate the amount of energy to a desired level.

Further, the temperature sensor 502 and the RF sensor 510 sends calculated information to the radio transmitting module 504. For example, the temperature sensor 502 determines temperature of the tissue surrounding the one or more medical grade susceptors 400 as 48° Celsius. In one embodiment, the heat measured by the temperature sensor 502 is produced by the infrared radiating heat that is generated at the one or more medical grade susceptors 400 in response to the output energy steered. For example, the RF sensor 510 determines the amount of energy imparted over the one or more medical grade susceptors 400 as 12.5 electron volts (ev). Successively, the radio transmitting module 504 transmits the information of the temperature of the tissue as 48° Celsius and amount of energy imparted over the one or more medical grade susceptors 400 as 12.5 ev to the receiver module 602.

Further, the receiver module 602 may send the collected information to the microcontroller 604. In one embodiment, the microcontroller 604 may be configured to process the received information and compare to a threshold value. In one embodiment, the threshold value may correspond to temperature of the one or more medical grade susceptors 400, and electromagnetic energy received by the one or more medical grade susceptors 400. Based upon the comparison, the microcontroller 604 may be configured to control the operation of the beam steering controller 606 by adjusting the pattern of interference. For example, the microcontroller 604 receives information of temperature of the tissue as 48° Celsius and compares to a threshold temperature of 46.5° Celsius. Further, the microcontroller 604 receives information of amount of energy imparted over the one or more medical grade susceptors 400 as 12.5 ev and compares with a threshold energy of 10.24 ev. Further, the microcontroller 604 upon comparing, generates one or more signals to operate the beam steering controller 606.

Further, the beam steering controller 606 may adjust the pattern of interference and coherence while broadcasting the millimeter waves to adjust and regulate the amount of energy to a desired level, based upon the generated one or more signals by the microcontroller 604. For example, the beam steering controller 606 alters the interference pattern of the transmitting millimeter waves by reducing an axis of a main lobe. In one embodiment, the main lobe may be a single large lobe created in a radiation plot. Thereby, by reducing the axis of the main lobe, the concentration of the imparting of the millimeter wave reduces, thereby decreasing the temperature from 48° Celsius to 46.5° Celsius. This ensures precise delivery of a sufficient and desired level of thermal energy to achieve beneficial clinical outcomes. By communicating the determining information about the temperature and amount of energy received, the one or more medical grade susceptors 400 are capable of more precise beam steering and energy application over the target tissue to achieve a level of temperature increase via a resulting feedback loop from the beam steering controller 606. In one embodiment, the feedback loop may be the one or more signals generated by the microcontroller 604 to alter the interference pattern of the mm wave.

While the specification has been described in detail with respect to specific embodiments of the invention, it will be appreciated that those skilled in the art, upon attaining an understanding of the foregoing, may readily conceive of alterations to, variations of, and equivalents to these embodiments. Any of the method steps discussed above can be conducted by a processor operating with a computer-readable non-transitory medium storing instructions for those method steps. The computer-readable medium may be memory within a personal user device or a network accessible memory. Although examples in the disclosure were generally directed to mmWave integrated circuits, similar approaches could utilize any source of mmWave energy such as mmWave transmitters that are not integrated on a single chip. Furthermore, while the examples in the disclosure were generally directed to mmWave radio frequency energy, the medical grade implantable susceptors and targeting techniques described herein could be applied to alternative sources of radio frequency energy such as high frequency, super high frequency, ultra-high frequency, and microwave energy. These and other modifications and variations to the present invention may be practiced by those skilled in the art, without departing from the scope of the present invention, which is more particularly set forth in the appended claims.

What is claimed is:

1. A system for hyperthermia-based anti-cancer treatments comprising:
an array of millimeter wave amplifier integrated circuits having an output energy;
one or more medical grade implantable susceptors, the one or more medical grade implantable susceptors including one or more radio frequency transmitters; and
a beam steering controller for the array of millimeter wave amplifier integrated circuits that is configured to steer the output energy of the array of millimeter wave amplifier integrated circuits into the one or more medical grade implantable susceptors, the beam steering controller for the array of millimeter wave amplifier integrated circuits being configured to steer the output energy using information from the one or more radio frequency transmitters.

2. The system of claim 1, wherein:
the output energy is a total output energy of the array of millimeter wave amplifier integrated circuits;
the beam steering controller for the array of millimeter wave amplifier integrated circuits is configured to steer at least 97% of the total output energy of the array of millimeter wave amplifier integrated circuits into the one or more medical grade implantable susceptors; and
the output energy is millimeter wave energy with a frequency of 30 to 220 gigahertz.

3. The system of claim 2, wherein:
the array of millimeter wave amplifier integrated circuits is an array of D band amplifiers.

4. The system of claim 1, wherein:
the output energy is electromagnetic wave energy with frequencies between 20 gigahertz and one terahertz.

5. The system of claim 1, wherein:
the one or more medical grade implantable susceptors include one or more temperature sensors; and
the beam steering controller for the array of millimeter wave amplifier integrated circuits is configured to adjust the output energy using information from the one or more temperature sensors.

6. The system of claim 5, wherein:
the one or more medical grade implantable susceptors include one or more wireless inductive power sources for the one or more radio frequency transmitters and the one or more temperature sensors; and
the one or more wireless inductive power sources are configured to charge using the output energy.

7. The system of claim 1, wherein the one or more medical grade implantable susceptors each comprise:
a susceptor body formed of one of stainless steel and titanium;
a temperature sensor connected to the susceptor body;
a radio frequency transmitter of the one or more radio frequency transmitters, the radio frequency transmitter being connected to the susceptor body;
a wireless inductive power source for the temperature sensor and the radio frequency transmitter; and
a polymer coating for the radio frequency transmitter, temperature sensor, and wireless inductive power source.

8. A hyperthermia-based anti-cancer method comprising:
sub-dermally implanting one or more medical grade implantable susceptors, the one or more medical grade implantable susceptors including one or more radio frequency transmitters;
generating, using an array of millimeter wave amplifier integrated circuits, an output energy;
transmitting information from the one or more radio frequency transmitters to a beam steering controller; and
steering, in a steering step and using the beam steering controller for the array of millimeter wave amplifier integrated circuits, the output energy of the array of millimeter wave amplifier integrated circuits into the one or more medical grade implantable susceptors, wherein steering the output energy uses the information from the one or more radio frequency transmitters.

9. The hyperthermia-based anti-cancer method of claim 8, further comprising:
generating infrared radiating heat energy at the one or more medical grade implantable susceptors in response to the steering step; and
causing tumor cell denaturation using the infrared radiating heat energy.

10. The hyperthermia-based anti-cancer method of claim 8, further comprising:
generating convection heat energy at the one or more medical grade implantable susceptors in response to the steering step; and
causing tumor cell denaturation using the convection heat energy.

11. The hyperthermia-based anti-cancer method of claim 8, wherein:
the output energy is a total output energy of the array of millimeter wave amplifier integrated circuits;
at least 97% of the total output energy of the array of millimeter wave amplifier integrated circuits is steered into the one or more medical grade implantable susceptors in the steering step; and
the output energy is millimeter wave energy with a frequency of 30 to 220 gigahertz.

12. The hyperthermia-based anti-cancer method of claim 11, wherein:
the array of millimeter wave amplifier integrated circuits is an array of D band amplifiers.

13. The hyperthermia-based anti-cancer method of claim 8, wherein:
the output energy is electromagnetic wave energy with frequencies between 20 gigahertz and one terahertz.

14. The hyperthermia-based anti-cancer method of claim 8, further comprising:
minimizing application of the output energy to healthy tissue using the information.

15. The hyperthermia-based anti-cancer method of claim 8, wherein:
the one or more medical grade implantable susceptors include one or more temperature sensors;
the hyperthermia-based anti-cancer method further comprises transmitting temperature information from the one or more radio frequency transmitters to the beam steering controller; and
the hyperthermia-based anti-cancer method further comprises adjusting the output energy, using the beam steering controller and the temperature information from the one or more radio frequency transmitters.

16. The hyperthermia-based anti-cancer method of claim 15, further comprising:
targeting one or more target temperatures for the one or more medical grade implantable susceptors during the adjusting.

17. The hyperthermia-based anti-cancer method of claim 8, wherein:
the one or more medical grade implantable susceptors include one or more temperature sensors;
the hyperthermia-based anti-cancer method further comprises transmitting temperature information from the one or more radio frequency transmitters to the beam steering controller; and
the hyperthermia-based anti-cancer method further comprises steering the output energy, using the beam steering controller and the temperature information from the one or more radio frequency transmitters.

18. The hyperthermia-based anti-cancer method of claim 10, wherein the one or more medical grade implantable susceptors each comprise:
a susceptor body formed of one of stainless steel and titanium;
a temperature sensor connected to the susceptor body;
a radio frequency transmitter of the one or more radio frequency transmitters, the radio frequency transmitter being connected to the susceptor body;
a wireless inductive power source for the temperature sensor and the radio frequency transmitter; and
a polymer coating for the radio frequency transmitter, temperature sensor, and wireless inductive power source.

* * * * *